United States Patent [19]

Wiley

[11] Patent Number: 5,019,105
[45] Date of Patent: May 28, 1991

[54] ACETABULAR CUP PROSTHESIS ASSEMBLY

[75] Inventor: Roy C. Wiley, North Webster, Ind.

[73] Assignee: Biomet, Inc., Warsaw, Ind.

[21] Appl. No.: 388,932

[22] Filed: Aug. 3, 1989

[51] Int. Cl.⁵ .............................................. A61F 2/30
[52] U.S. Cl. ........................................................ 623/22
[58] Field of Search ...................... 623/16, 18, 19, 20, 623/21, 22, 23

[56] References Cited

U.S. PATENT DOCUMENTS

| | | | |
|---|---|---|---|
| Re. 28,895 | 7/1976 | Noiles | 623/22 |
| 3,717,932 | 2/1973 | Brainin . | |
| 3,813,699 | 6/1974 | Giliberty . | |
| 3,818,512 | 6/1974 | Shersher . | |
| 3,840,904 | 10/1974 | Tronzo . | |
| 3,863,273 | 2/1975 | Averill . | |
| 3,978,528 | 9/1976 | Crep . | |
| 4,077,070 | 3/1978 | Sivash . | |
| 4,135,517 | 1/1979 | Reale . | |
| 4,172,296 | 10/1979 | D'Errico . | |
| 4,206,517 | 6/1980 | Pappas et al. . | |
| 4,241,463 | 12/1980 | Khovaylo . | |
| 4,380,090 | 4/1983 | Ramos . | |
| 4,408,360 | 10/1983 | Keller . | |
| 4,410,295 | 10/1983 | Ersoy et al. . | |
| 4,619,658 | 10/1986 | Pappas et al. . | |
| 4,624,674 | 11/1986 | Pappas et al. . | |
| 4,670,015 | 6/1987 | Freeman . | |
| 4,676,799 | 6/1987 | Legrand . | |
| 4,718,911 | 1/1988 | Kenna . | |
| 4,770,658 | 9/1988 | Geremakis | 623/22 |
| 4,795,469 | 1/1989 | Oh | 623/22 |

FOREIGN PATENT DOCUMENTS

| | | |
|---|---|---|
| 2039731 | 2/1971 | Fed. Rep. of Germany . |
| 1943598 | 3/1971 | Fed. Rep. of Germany . |
| 2301810 | 1/1973 | Fed. Rep. of Germany . |
| 2323456 | 5/1973 | Fed. Rep. of Germany . |
| 2340734 | 2/1975 | Fed. Rep. of Germany ........ 623/22 |
| 2628530 | 12/1976 | Fed. Rep. of Germany . |
| 2714387 | 11/1977 | Fed. Rep. of Germany . |
| 2826690 | 2/1979 | Fed. Rep. of Germany . |
| 1362187 | 7/1974 | United Kingdom . |
| 1415736 | 11/1975 | United Kingdom . |

Primary Examiner—David J. Isabella
Attorney, Agent, or Firm—Barnes & Thornburg

[57] ABSTRACT

An acetabular cup prosthesis assembly has an outer shell, a bearing insert, a locking collar, and a locking ring. The bearing insert is retained within the outer shell, which has a generally smooth, hemispherical outer surface. The bearing insert is adapted to receive the femoral head of a hip prosthesis. An opening of the insert has a first diameter which is smaller than the diameter of the femoral head, and is elastically expandable to a second diameter to allow for passage of the femoral head through the opening. The locking collar is movable from a disengaged position to an engaged position adjacent the bearing insert to prevent the opening from expanding to the second diameter so as to lock the femoral head in position within the insert. The locking ring is disposed within a first circumferential groove in the inner surface of the outer shell, and serves to maintain the locking collar in position adjacent the bearing insert. The outer shell, the bearing insert, and the locking ring may be assembled into a sub-assembly which may be separately packed and sterilized for use by an orthopedic surgeon. The sub-assembly and locking collar form a two-component system which is easily manipulated during the implantation procedure.

31 Claims, 4 Drawing Sheets

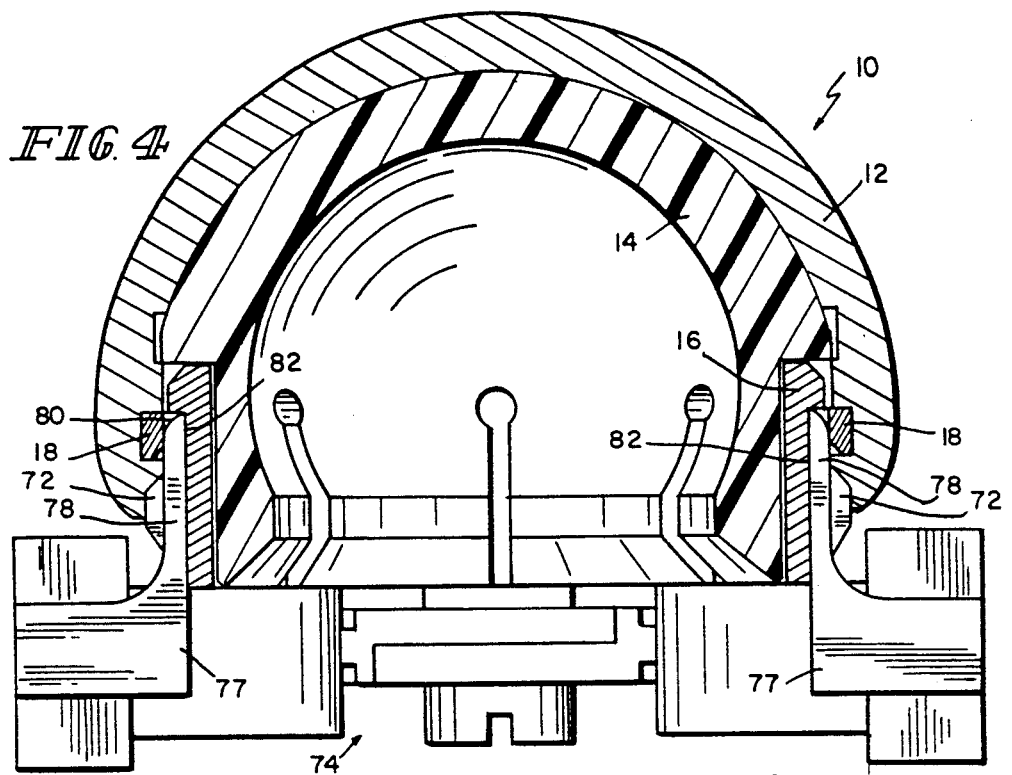
FIG. 4
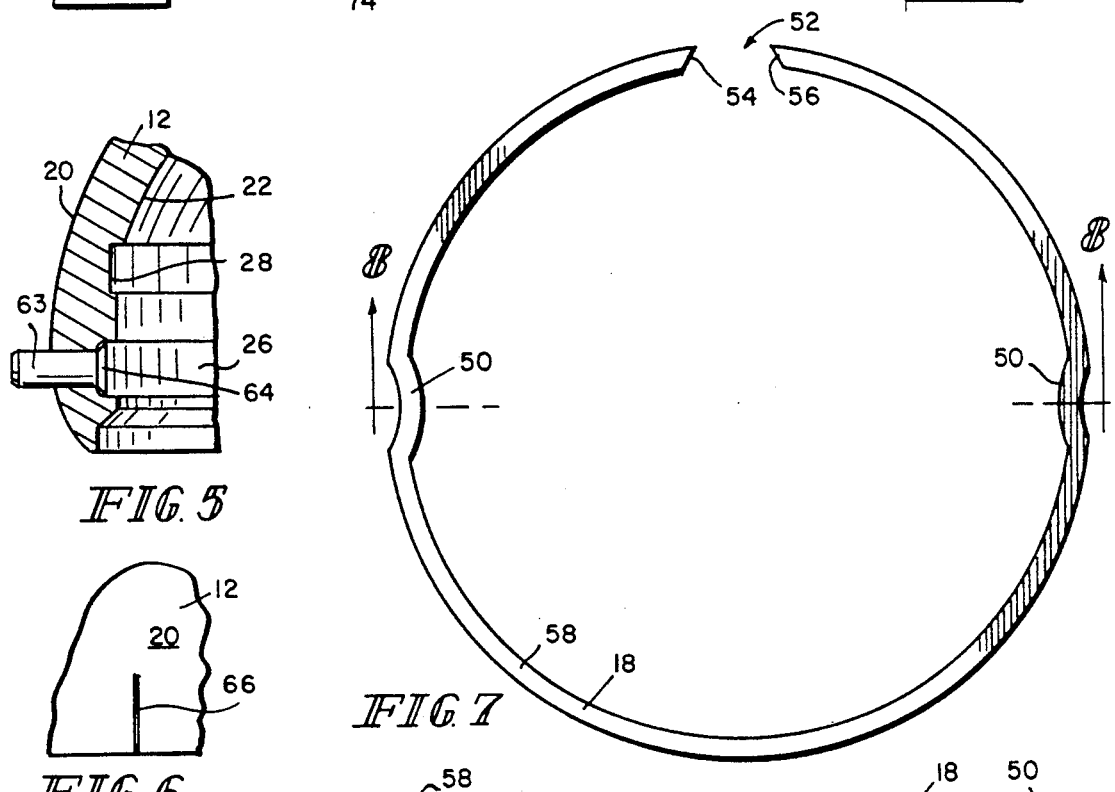
FIG. 5
FIG. 6
FIG. 7
FIG. 8

ACETABULAR CUP PROSTHESIS ASSEMBLY

BACKGROUND AND SUMMARY OF THE

The present invention relates generally to acetabular cup prostheses and, more particularly, to an improved acetabular cup prosthesis of the type having a highly polished, smooth, spherical outer surface.

Acetabular cup prostheses which feature an outer shell having a smooth, spherical outer surface and a bearing insert having a smooth, spherical inner surface are known. The smooth outer surface of the outer shell fits within the natural acetabulum, and is free to move within that cavity. The smooth, inner surface of the bearing insert is fitted over the head of the femoral component of a hip prosthesis in a manner which produces three-degree freedom of movement between the bearing insert and the head. The double articulation provided by this type of prosthetic acetabular component is advantageous in providing nearly anatomical ranges of motion to prosthetic joints in certain cases, and is often less destructive of the natural acetabulum. This type of acetabular cup prosthesis is often referred to as a "bipolar" prosthesis due to the freedom of movement which exists between the femoral head and bearing insert, and the smooth outer shell and the acetabular cavity Bipolar acetabular cup prostheses are shown and described in several prior U.S. patents, including U.S. Pat. Nos. 3,813,699 to Giliberty, 3,863,273 to Averill, 4,172,296 to D'Errico, 4,241,463 to Khovaylo, 4,408,360 to Keller, 4,619,658 to Pappas et al., 4,676,799 to Legrand, and 4,718,911 to Kenna. Several of these patents discuss the workings of such joints and the conditions under which they are most often used in replacing defective anatomical joints. To the extent that these discussions are helpful in the appreciation and understanding of the present invention, these disclosures are hereby incorporated into the present disclosure by this reference thereto.

In the design of a bipolar acetabular cup prosthesis, it is necessary to consider a number of factors, including the ease with which a particular prosthesis design can be assembled and/or disassembled under the conditions normally found in the orthopedic operating room. Moreover, the assembled prosthesis must provide some degree of resistance to dislocation and separation of components under the stresses and ranges of motion to which prosthetic joints are commonly exposed.

It is an object of the present invention to provide an improved bipolar acetabular cup prosthesis assembly which addresses the design considerations noted above.

More particularly, it is an object of the present invention to provide a bipolar acetabular cup prosthesis which provides for a high degree of resistance to dislocation and separation of the components thereof.

Another object of the present invention is to provide a bipolar acetabular cup prosthesis assembly which is relatively easy to assemble and manipulate under typical operating room conditions.

Yet another object of the present invention is to provide a bipolar acetabular cup prosthesis assembly which is easy to disassemble in the event revision of the prosthetic joint becomes necessary.

Still yet another object of the present invention is to provide a bipolar acetabular cup prosthesis assembly in which several of the components may be assembled into a sub-assembly prior to the installation procedure, thus reducing the number of individual components which must be handled by the surgeon and facilitating and simplifying the overall installation process.

These and other objects of the invention are attained in an acetabular cup prosthesis assembly which includes an outer shell, a bearing insert, means for retaining the bearing insert within the outer shell, a locking collar, and a locking ring. The outer shell of the assembly has a generally smooth hemispherical outer surface, an inner surface, an opening defined by a peripheral edge surface which joins the outer and inner surfaces, and a first circumferential groove formed in the inner surface. The bearing insert is adapted to be received within the opening in the outer shell. The insert has an outer surface, an inner surface, and an opening defined by a peripheral edge surface which joins the outer and inner surfaces. The inner surface and opening are adapted to receive the femoral head of a hip prosthesis. The opening has a first diameter which is smaller than a diameter of the femoral head, and is elastically expandable to a second diameter to allow for passage of the femoral head through the opening. The locking collar is movable from a disengaged position to an engaged position adjacent a portion of the outer surface of the bearing insert to prevent the opening from expanding to the second diameter so as to allow the femoral head to be locked into place within the insert. The locking ring is disposed within the first circumferential groove in the inner surface of the outer shell. At least a portion of the locking ring protrudes outwardly from the groove beyond the inner surface of the shell so as to interact with a portion of the locking collar to secure the collar in the engaged position adjacent the outer surface of the bearing insert. The protruding portion of the locking ring is elastically deformable inwardly into the groove so as to allow the locking collar to be selectively moved to the disengaged and engaged positions.

In one embodiment of the invention, the means for retaining the bearing insert within the opening in the outer shell comprises a second circumferential groove formed in the inner surface of the outer shell, and means formed in the outer surface of the bearing insert extending into the second groove for retaining the bearing insert within the opening in the shell. The means formed on the outer surface of the bearing insert preferably comprises an outwardly extending lip having a generally horizontal surface which extends into the second groove and which interacts with a surface of the groove to retain the bearing insert within the opening in the shell. Although the bearing insert and outer shell can be designed and dimensioned so as to allow the insert to be inserted into the outer shell by hand, it is preferred to use a mechanical means or operation to join these two components to decrease the likelihood of their unintended separation. One technique involves dimensioning the bearing insert to be slightly larger than the size that could otherwise be inserted into the outer shell, cooling the oversized bearing insert with liquid nitrogen to cause the outer dimensions thereof to shrink, and inserting the cooled bearing insert into the outer shell to allow it to expand in the assembled position.

In one embodiment of the invention, the protruding portion of the locking ring comprises a plurality of tabs formed in generally opposing relation on opposite sides of the locking ring. This embodiment further comprises means for preventing rotational movement of the locking ring so as to maintain the orientation of the tabs relative to the outer shell. The means for preventing rotational movement of the locking ring comprises a split in the ring, and means secured to the outer shell and protruding into the first circumferential groove so as to engage surfaces of the split. The means secured to the outer shell comprises a pin extending from the outer surface to the inner surface of the outer shell and into the first circumferential groove. Indicia are provided on the outer surface of the outer shell to indicate the orientation of the protruding tabs of the locking ring relative to the outer shell. A plurality of slots are provided in the locking collar to facilitate access to the plurality of tabs on the locking ring.

The protruding portion of the locking ring has an inwardly facing surface which interacts with an outwardly facing surface of the locking collar to secure the collar in the engaged position adjacent the outer surface of the bearing insert. The protruding portion of the locking ring further has an outwardly facing beveled surface which interacts with a beveled surface on the locking collar to facilitate deformation of the protruding portion inwardly into the first circumferential groove to allow the locking collar to be moved into the engaged position adjacent the outer surface of the bearing insert.

One embodiment of the present invention further comprises an extraction tool for elastically deforming the locking means when the locking collar is in the engaged position, and for interacting with the locking collar to facilitate movement of the collar to the disengaged position. The extraction tool includes a portion which is insertable within slots in the locking collar to engage and deform the protruding portions of the locking ring. A roughened, grooved, or knurled surface is provided to increase the coefficient of friction between the extraction tool and locking collar to further facilitate disengagement of the collar from the assembly.

The outer shell of the acetabular cup prosthesis of the present invention is preferably formed of a biologically compatible metal alloy, such as a cobalt-chromium alloy. Other materials, such as titanium alloys and ceramics, may also be used. The bearing insert and locking collar are preferably formed of ultra-high molecular weight polyethylene (UHMWPE). The locking ring is preferably formed of UHMWPE or high density polyethylene (HDPE).

In an especially preferred embodiment of the present invention, the outer shell, bearing insert, and locking ring may be assembled into a sub-assembly which may be separately packed and sterilized for use by the surgeon at the time of installation. This sub-assembly and the locking collar thus form a two-component system which is easily manipulated by the surgeon to simplify and facilitate the installation process.

Other objects, advantages and novel features of the present invention will become apparent from the following detailed description of the invention when considered in conjunction with the accompanying drawings.

BRIEF DESCRIPTION OF THE DRAWINGS

FIG. 4 shows a cross-sectional side view of an acetabular cup prosthesis assembly constructed in accordance with a preferred embodiment of the present invention immediately prior to disengagement of the locking collar.

FIG. 5 shows a partial cross-sectional view of an outer shell of an acetabular cup prosthesis assembly.

FIG. 6 shows a partial view of the outer surface of an outer shell of an acetabular cup prosthesis assembly.

FIG. 7 shows a top view of a preferred embodiment of a locking ring which may be used with an acetabular cup prosthesis assembly constructed in accordance with a preferred embodiment of the present invention.

FIG. 8 shows a cross-sectional side view of the locking ring of FIG. 7, taken along line 8—8 of FIG. 7.

DETAILED DESCRIPTION OF THE DRAWINGS

Figure 1:
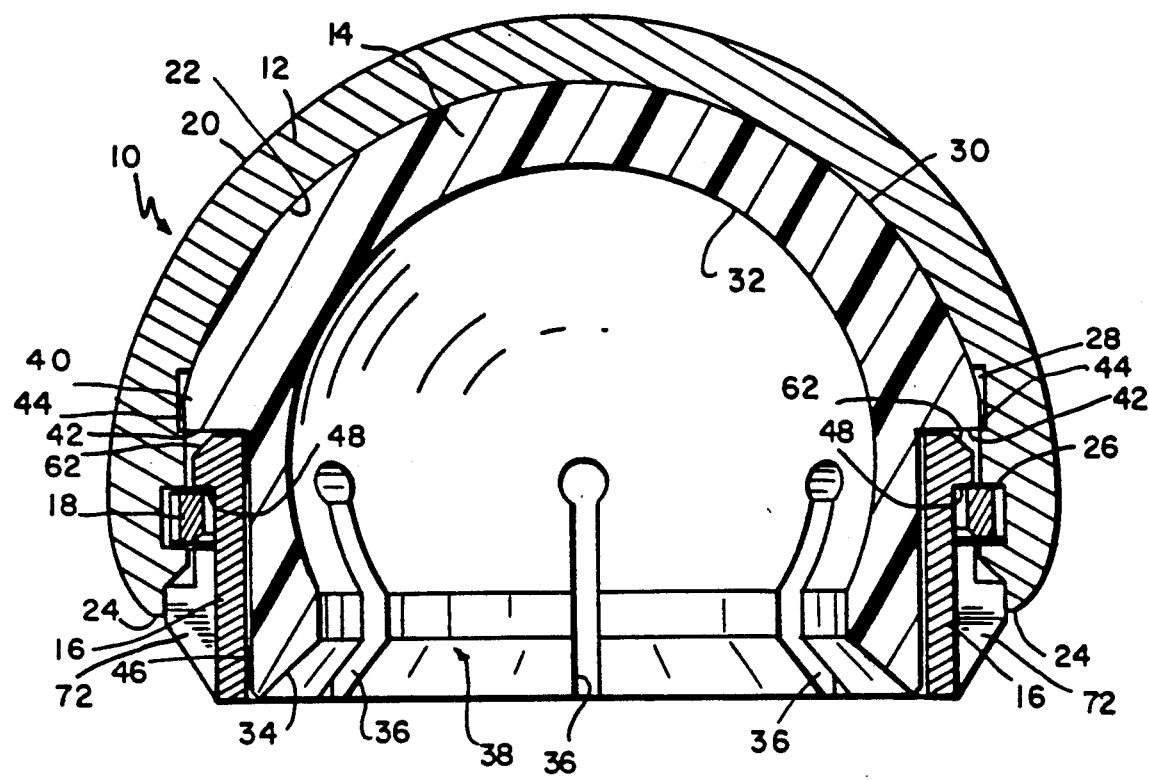
FIG. 1 shows a cross-sectional side view of an acetabular cup prosthesis assembly constructed in accordance with a preferred embodiment of the present invention.

FIGS. 1–8 illustrate an acetabular cup prosthesis assembly constructed in accordance with the principals of the present invention. FIG. 1 shows a cross-sectional side view of an acetabular cup prosthesis assembly 10. Assembly 10 includes an outer shell 12, a bearing insert 14, a locking collar 16 and a locking ring 18. Outer shell 12 has a generally smooth hemispherical outer surface 20 and an inner surface 22. Outer shell 12 is generally cup shaped, with the opening of the "cup" being defined by a peripheral edge surface 24 which joins outer surface 20 and inner surface 22.

Outer shell 12 further comprises a first circumferential groove 26 in which locking ring 18 is disposed. Locking ring 18 is illustrated in additional detail in FIGS. 7 and 8, and is discussed more fully below. Outer shell 12 has a second circumferential groove 28 which, in the preferred embodiment of the invention illustrated, serves as part of the means for retaining bearing insert 14 within the cup-shaped opening and adjacent inner wall 22 of outer shell 12.

Outer shell 12 includes additional features (i.e., a pin which extends into first circumferential groove 26 to prevent rotation of locking ring 18 and indicia etched on outer surface 20) which are not visible in FIG. 1, and which are discussed below in connection with FIGS. 5 and 6. Outer shell 12 is preferably formed of a biologically compatible metal alloy, such as a cobalt-chromium alloy, which is polished smooth and buffed to provide a smooth finish on outer surface 20. Alternative materials, such as titanium alloys and ceramics, may also be used in forming outer shell 12.

Acetabular cup prosthesis assembly 10 further includes bearing insert 14 which is received within the opening of and retained adjacent inner surface 22 of outer shell 12. Bearing insert 14 has an outer surface 30, an inner surface 32, and a cup-shaped opening which is defined at its entrance by a peripheral edge surface 34 which joins outer surface 30 and inner surface 32. Inner surface 32 and the cup-shaped opening of insert 14 are adapted to receive the femoral head of a hip prosthesis (illustrated in dashed lines in FIG. 2). The upper half of bearing insert 14 (as illustrated in FIG. 1) is generally spherical in shape, while the lower half of insert 14 is generally cylindrical. A plurality of longitudinally extending slots 36 are provided in the cylindrical portion 46 of bearing insert 14. Insert 14 is formed of a material, such as ultra-high molecular weight polyethylene (UHMWPE), which will allow some flexing of the "leaves" formed by the longitudinal slots. The entrance to the cup-shaped opening in insert 14 has a first relatively small diameter in the entrance area generally indicated by arrow 38 which is smaller than the diameter of the femoral head (39 in FIG. 2) of the hip prosthesis. The relative flexibility of the material of which bearing insert 14 is formed and the longitudinal slots 36 combine to make entrance 38 to the opening elastically expandable to a second diameter which allows for passage of the femoral head through entrance 38 and into (or out of) the opening.

Bearing insert 14 has an outwardly extending lip 40 which, in the embodiment illustrated, is formed in outer surface 30 in the general area of transformation from the spherical to cylindrical portions of insert 14. Lip 40 extends into second circumferential groove 28 in inner surface 22 of outer shell 12. A peripheral edge portion 42 of lip 40 interacts with a side surface 44 of groove 28 to serve as a means for retaining bearing insert 14 in position within the cup-shaped opening of outer shell 12. The extent of the interaction or overlap of surfaces 42 and 44, and the relative resiliency of the materials from which outer shell 12 and/or bearing insert 14 are formed, may combine to allow insert 14 to be inserted in its final retained position by hand. However, in most instances, it is preferred to have a tighter mechanical fit between outer shell 12 and bearing insert 14 to assure that these components do not unintentionally disengage during usage. One technique for achieving such a fit is to dimension outer shell 12 and bearing insert 14 such that there is a high degree of interference between the two components, chill bearing insert 14 with liquid nitrogen to shrink the outer dimensions thereof, and insert bearing insert 14 into outer shell 12 by manual or mechanical means in its chilled condition to allow it to expand into a tight mechanical fit with outer shell 12. Alternative arrangements for retaining insert 14 in position, such as the provision of a groove in outer surface 30 of insert 14 and a lip or projection on inner surface 22 of outer shell 12, may also be used.

After femoral head 39 is positioned within the cup-shaped opening of bearing insert 14, locking collar 16 is moved from a disengaged position (shown in FIG. 2) to an engaged position (shown in FIG. 1) adjacent the generally cylindrical portion 46 of outer surface 30 of insert 14. Locking collar 16 prevents entrance 38 of the cup-shaped opening from expanding to the second relatively larger diameter which allows femoral head 39 to pass therethrough. Thus, locking collar 16 allows femoral head 39 to be locked into place within the opening of insert 14. Locking collar 16 is preferably formed of a plastic material, such as UHMWPE.

In the embodiment illustrated, locking collar 16 is secured in the engaged position shown in FIG. 1 by locking ring 18. Locking ring 18 is preferably disposed in first circumferential groove 26 in inner surface 22 of outer shell 12. At least a portion of locking ring 18 protrudes outwardly from groove 26 beyond inner surface 22 of shell 12 so as to interact with a portion (outwardly facing surface 48) of locking collar 16 to secure collar 16 in the engaged position adjacent surface 46 of insert 14.

FIGS. 7 and 8 show top and side cross-section views, respectively, of a preferred embodiment of locking ring 18. With reference to FIG. 7, the protruding portions of locking ring 18 which interact with surface 48 of locking collar 16, in this preferred embodiment, comprise two tabs 50 formed in generally opposing relation on two sides of locking ring 18. Additional tabs may be provided as necessary. An additional feature of locking ring 18 which is not visible in FIG. 1, but which can be seen in FIG. 7, is split 52 which is provided for a plurality of reasons. First, the existence of split 52 allows the overall diameter of ring 18 to be elastically compressed to facilitate insertion of ring 18 into groove 26. Secondly, split 52 is used for preventing rotational movement of locking ring 18 so as to maintain the orientation of tabs 50 relative to outer shell 12. This feature is discussed in additional detail below in connection with FIG. 5.

FIG. 8 shows a cross-sectional side view of the locking ring of FIG. 7, taken along line 8—8 of FIG. 7. This view illustrates the cross-sectional shape of locking ring 18 in the area of tabs 50, and is similar in this respect to the views of locking ring 18 shown in FIGS. 1 and 2. The cross-sectional shape of tabs 50 includes a generally horizontal peripheral surface 58 which interacts with surface 48 of locking collar 16 to retain locking collar 16 in the engaged position. Locking ring 18 further has a beveled surface 60 which interacts with a beveled surface 62 on locking collar 16 to facilitate deformation of tabs 50 into groove 26 as locking collar 16 is moved from the disengaged into the engaged position. Beveled surface 60 also interacts with a portion of an extraction tool to facilitate deformation of locking ring 18 and removal of locking collar 16, as discussed more fully below.

As noted, locking ring 18 is provided with a split 52 which is used for preventing rotational movement of locking ring 18 so as to maintain the orientation of tabs 50 relative to outer shell 12. This is accomplished by securing to the outer shell a device which protrudes into first circumferential groove 26, and which engages surfaces 54 and 56 of split 52. In one preferred embodiment of the invention, this device is constructed as a pin 63 which is illustrated in detail in FIG. 5. FIG. 5 shows a portion of outer shell 12 with pin 63 positioned in a hole drilled through outer shell 12 at the level of first groove 26. Pin 63 is subsequently welded or otherwise secured to outer shell 12, and the portion of pin 63 which extends beyond outer surface 20 is removed before outer surface 20 is polished and buffed. The "head" portion 64 of pin 63 which extends into first circumferential groove 26 is beveled so as to "mate" with surfaces 54 and 56 of locking ring 18. This arrangement assures that locking ring 18 will remain in a fixed orientation after initial installation in outer shell 12.

FIG. 6 shows a portion of outer surface 20 of outer shell 12 immediately adjacent the general location of one of tabs 50 of locking ring 18. As indicated in FIG. 6, an etched line 66 is provided on outer surface 20 to serve as an indicia of the location of each of the tabs 50. The presence of line 66 on surface 20 facilitates deformation of tabs 50 and extraction of locking collar 16, as is explained more fully below.

Figure 2:
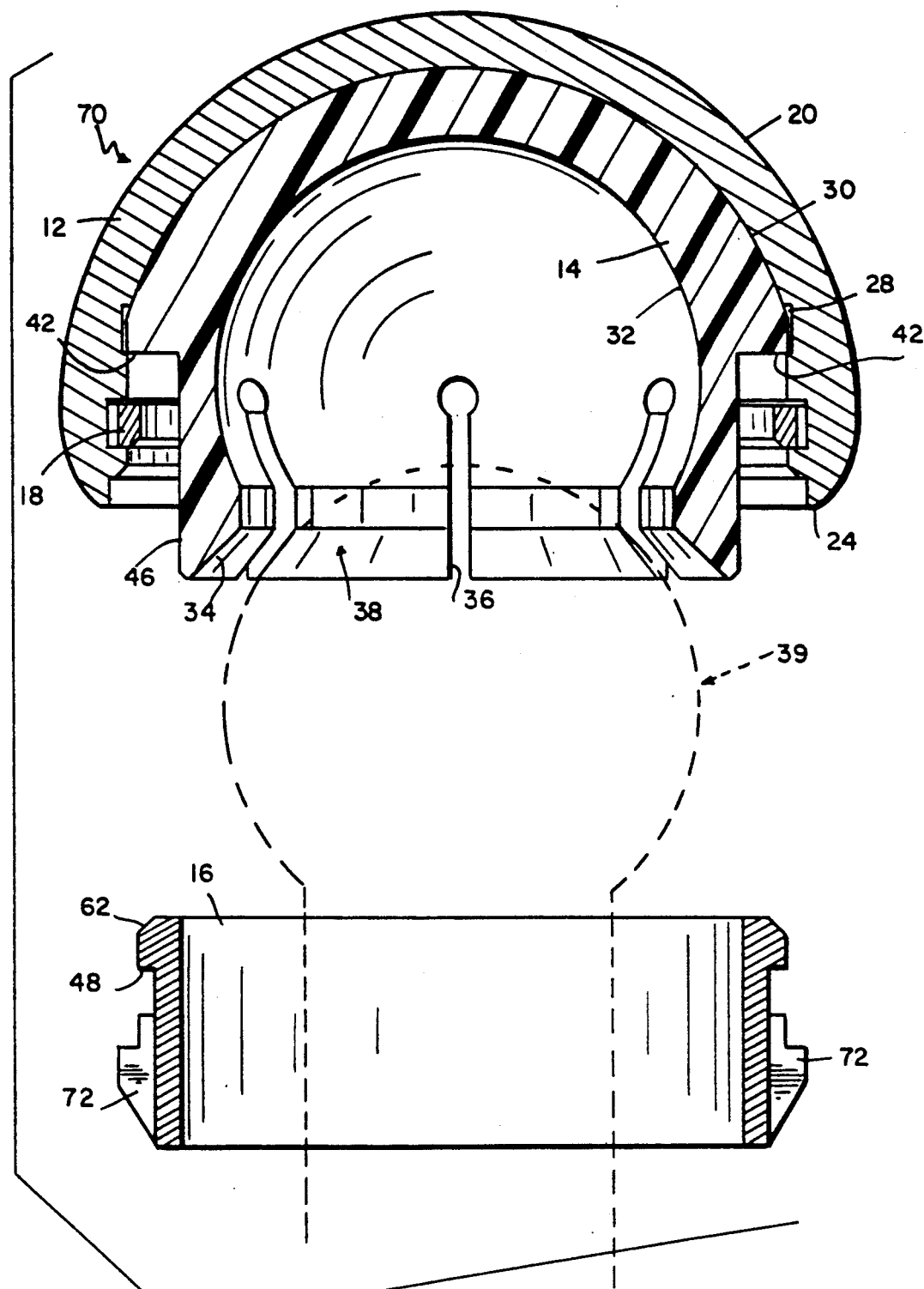
FIG. 2 shows a cross-sectional side view of a sub-assembly and locking collar of an acetabular cup prosthesis constructed in accordance with a preferred embodiment of the present invention.

FIG. 2 shows a cross-sectional side view of an acetabular cup prosthesis sub-assembly and locking collar of the type discussed in connection with the remainder of the drawing figures. Where appropriate, like reference numbers have been used for purpose of simplicity and clarity. FIG. 2 illustrates an important advantage of the present invention which may not be readily apparent from the remaining figures. That advantage lies in the fact that outer shell 12, inner bearing 14 and locking ring 18 may be configured in a sub-assembly 70 which may then be sterilized and packed for ultimate use by an orthopedic surgeon in the operating room. The remaining component of assembly 10 (i.e., locking collar 16) is positioned over head 39 of a femoral component of a hip prosthesis (the disengaged position), and is moved in the direction of the arrows shown in FIG. 2 to the engaged position after head 39 has been inserted into the opening in bearing insert 14. Locking collar 16 and locking ring 18 are preferably designed so that locking collar 16 may be moved into the engaged position manually (i.e., by application of digital pressure) by the surgeon. When locking collar 16 has been "snapped" into the engaged position, as illustrated in FIG. 1, head 39 is securely locked in position within the opening of bearing insert 14.

Figure 3:
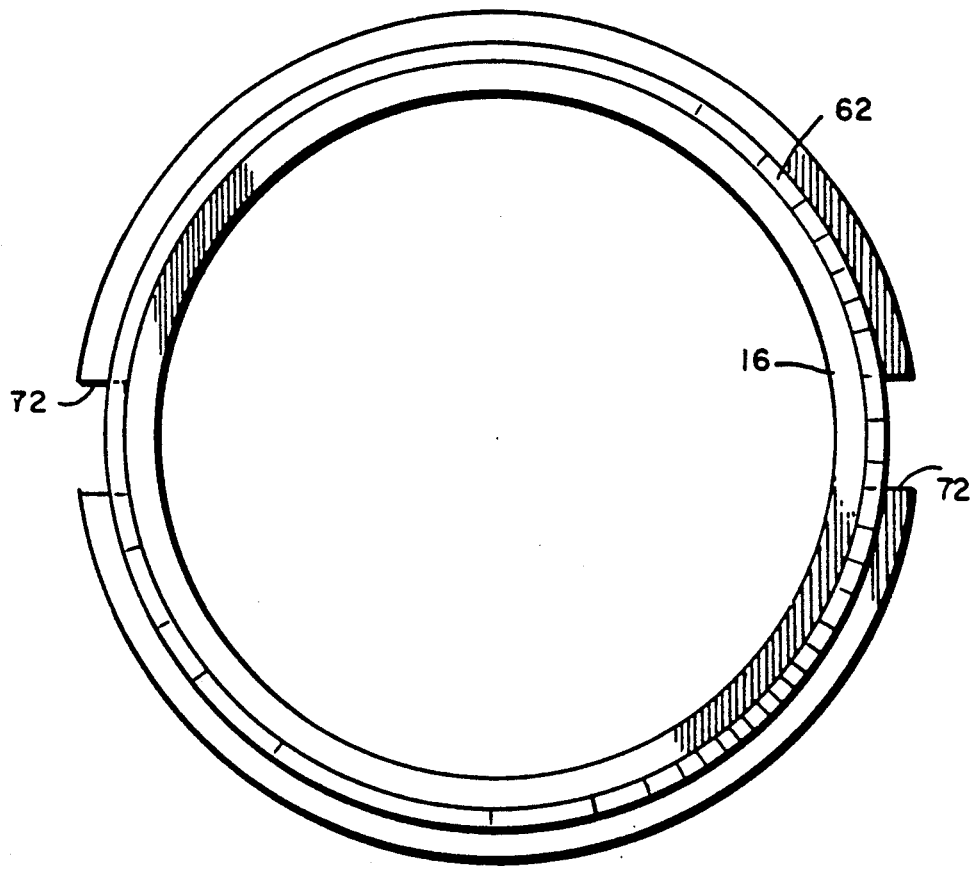
FIG. 3 shows a top view of the locking collar of FIG. 2.

FIG. 3 shows a top view of locking collar 16. FIG. 3 shows an additional feature of locking collar 16 that, while visible in FIGS. 1 and 2, is more clearly illustrated by this top view. This feature is the provision of two slots 72 in the outer- and lower-most portion of locking collar 16 (as viewed in FIG. 2). Slots 72 are intended to be aligned with tabs 50 of locking ring 18 to facilitate insertion of an extraction tool (discussed below) to aid in the disengagement of locking collar 16 from sub-assembly 70. Slots 72 are preferably aligned with etched line 66 on outer surface 20 of outer shell 12 prior to moving locking collar 16 into the engaged position. In the event locking collar 16 is subsequently rotated relative to sub-assembly 70, slots 72 can be re-aligned with line 66 prior to disengagement.

FIG. 4 shows a cross-sectional side view of acetabular cup prosthesis assembly 10 immediately prior to disengagement of locking collar 16. Again, like reference numerals are used where appropriate to simplify and clarify the present discussion. Removal of locking collar 16 is accomplished by insertion of extraction tool 74 into slots 72, as illustrated in FIG. 4. Tool 74, which is illustrated in additional detail in FIGS. 9 and 10, has two upstanding portions 78 which are designed for insertion into slot 72 to engage the elastically deformable tabs 50 of locking ring 18. Upstanding portions 78 deform tabs 50 as shown in FIG. 4 to disengage surfaces 48 and 58 of locking collar 16 and locking ring 18, respectively, so as to allow for removal of locking collar 16. A leading edge surface 80 of upstanding portion 78 of tool 74 is rounded or beveled to facilitate insertion of the tool by interaction with beveled surface 60 of locking ring 18. An end surface 82 (FIGS. 9 and 10) of portion 78 of tool 74 is roughened (for example, by providing grooves in surface 82) to increase the coefficient of friction between surface 82 and locking collar 16 so as to better grip collar 16 for extraction purposes.

Figure 9:
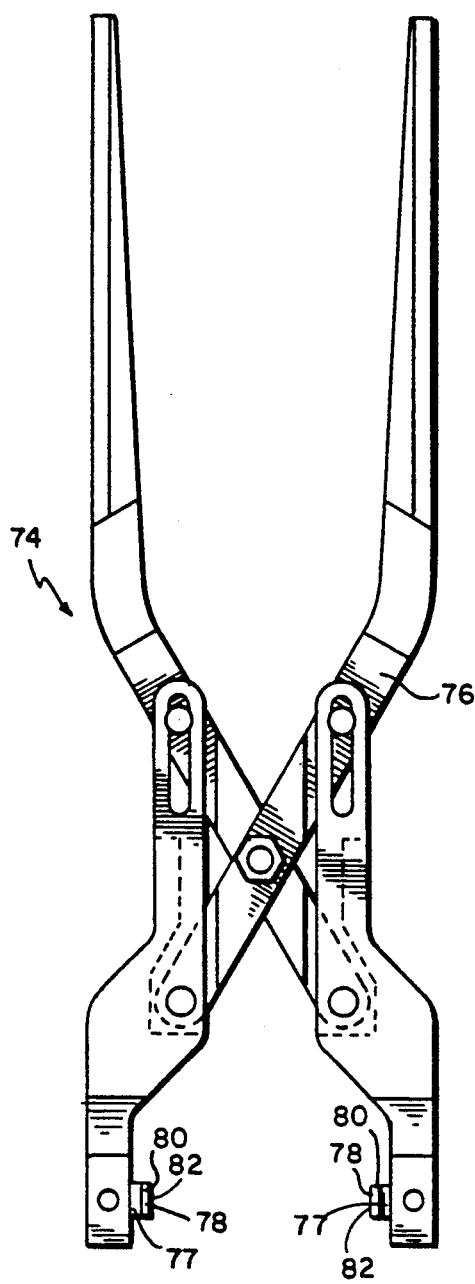
FIG. 9 shows a plan view of an extraction tool suitable for use with an acetabular cup prosthesis assembly constructed in accordance with a preferred embodiment of the present invention.
Figure 10:
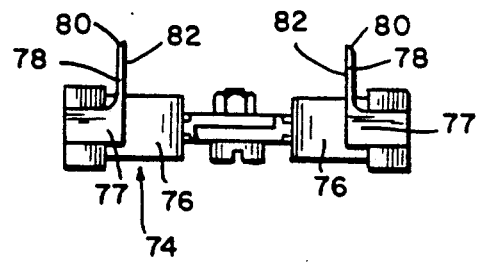
FIG. 10 shows an end view of the extraction tool shown in FIG. 9.

FIG. 9 shows a plan view of a preferred embodiment of extraction tool 74. Tool 74 includes a handle portion 76, to which is mounted a pair of finger-like elements 77. Handle 76 allows for adjustment of the distance between finger-like elements 77 to accommodate difference sizes of prostheses. Finger-like elements 77 are provided with upstanding portions 78 which are described above in reference to FIG. 4, and which are illustrated in the end view of FIG. 10.

From the preceding description of the preferred embodiment, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert; and locking means separable from said collar means, disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said collar means to be selectively moved to the disengaged and engaged positions.

2. An acetabular cup prosthesis according to claim 1, wherein said retaining means comprises a second circumferential groove formed in said inner surface of the outer shell, and further comprising lip means formed in the outer surface of the bearing insert and extending into said second groove for retaining the bearing insert within the opening in the shell.

3. An acetabular cup prosthesis according to claim 2, wherein said lip means formed in the outer surface of the bearing insert comprises an outwardly extending lip having a generally horizontal surface which extends into the second groove and which interacts with a surface of the groove to retain the bearing insert within the opening in the shell.

4. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert;

locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said collar means to be selectively moved to the disengaged and engaged positions; and second retaining means for preventing rotational movement of said locking ring in said first circumferential groove.

5. An acetabular cup prosthesis according to claim 4, wherein said second retaining means comprises a split in said locking means, and pin means secured to the outer shell and protruding into the first circumferential groove so as to engage surfaces of said split.

6. An acetabular cup prosthesis according to claim 5, wherein said pin means secured to the outer shell comprises a pin extending from the outer surface to the inner surface of the outer shell and into the first circumferential groove.

7. An acetabular cup prosthesis according to claim 1, wherein said protruding portion of said locking means has an inwardly facing surface which interacts with an outwardly facing surface of the collar means to secure said collar means in the engaged position adjacent the outer surface of the bearing insert, and an outwardly facing beveled surface to facilitate deformation of said protruding portion inwardly into the first circumferential groove.

8. An acetabular cup prosthesis according to claim 1, wherein said outer shell is formed of a biological compatible metal alloy.

9. An acetabular cup prosthesis according to claim 1, wherein said bearing insert is formed from ultra-high molecular weight polyethylene.

10. An acetabular cup prosthesis according to claim 1, wherein said collar means is formed from ultra-high molecular weight polyethylene.

11. An acetabular cup prosthesis according to claim 1, wherein said locking means is formed from one of a high density polyethylene and an ultra-high molecular weight polyethylene.

12. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert; and locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said collar means to be selectively moved to the disengaged and engaged positions;

wherein said protruding portion of said locking means comprises a plurality of tabs formed in generally opposing relation on said locking means.

13. An acetabular cup prosthesis according to claim 12, further comprising second retaining means for preventing rotational movement of said locking means so as to maintain the orientation of said tabs relative to the outer shell.

14. An acetabular cup prothesis assembly, comprising:

a sub-assembly which includes:
an outer shell having an outer surface and an inner surface;
a bearing insert having an outer surface, an inner surface, and an opening defined by an edge surface joining said outer and inner surfaces, said opening having a relatively small first diameter and being elastically expandable to a relatively larger second diameter;
retaining means for retaining the outer surface of the bearing insert adjacent the inner surface of the outer shell; and
locking means disposed on the inner surface of the outer shell, at least a portion of said locking means protruding outwardly from said inner surface of said shell, said portion being elastically deformable inwardly toward said inner surface; and collar means, separable from said locking means, movable from a disengaged position to an engaged position adjacent the outer surface of the bearing insert, for preventing said opening from expanding to said second diameter, said collar means interacting with the protruding portion of said locking means to secure the collar means in said engaged position adjacent the outer surface of the bearing insert.

15. An acetabular cup prosthesis assembly according to claim 14, wherein said outer shell has a first circumferential groove formed in the inner surface thereof, and wherein said locking means comprises a locking ring disposed in said first circumferential groove.

16. An acetabular cup prosthesis assembly, comprising:
   a sub-assembly which includes:
      an outer shell having an outer surface and an inner surface;
      a bearing insert having an outer surface, an inner surface, and an opening defined by an edge surface joining said outer and inner surfaces, said opening having a relatively small first diameter and being elastically expandable to a relatively larger second diameter;
      retaining means for retaining the outer surface of the bearing insert adjacent the inner surface of the outer shell; and
      locking means disposed on the inner surface of the outer shell, at least a portion of said locking means protruding outwardly from said inner surface of said shell, said portion being elastically deformable inwardly toward said inner surface; and
      collar means, movable from a disengaged position to an engaged position adjacent the outer surface of the bearing insert, for preventing said opening from expanding to said second diameter, said collar means interacting with the protruding portion of said locking means to secure the collar means in said engaged position adjacent the outer surface of the bearing insert;
      wherein said outer shell has a first circumferential groove formed in the inner surface thereof, and wherein said locking means comprises a locking ring disposed in said first circumferential groove; and
      second retaining means for preventing rotational movements of the locking ring so as to maintain the protruding portion of the ring in a fixed orientation relative to the outer shell.

17. An acetabular cup prosthesis assembly according to claim 16, wherein said second retaining means for preventing rotational movement of the locking ring comprises a split in said ring, and further comprising pin means in the first circumferential groove for engaging surfaces of said split to prevent rotation of the ring.

18. An acetabular cup prosthesis assembly according to claim 15, wherein said collar means has a beveled surface facing inwardly toward the inner surface of the outer shell, and a generally horizontal surface facing outwardly from the inner surface of the outer shell, and wherein said beveled surface interacts with a beveled surface of the protruding portion of the locking ring to facilitate elastic deformation of said portion when the collar means is moved into the engaged position adjacent the outer surface of the bearing insert, and wherein said generally horizontal surface interacts with a generally horizontal surface of the protruding portion of the locking ring when the collar means reaches the engaged position to retain the collar means in said position.

19. An acetabular cup prosthesis assembly according to claim 14, wherein said retaining means for retaining the bearing insert adjacent the inner surface of the outer shell comprises a second circumferential groove formed in the inner surface of the outer shell, and further comprising lip means formed in the outer surface of the bearing insert and extending into said second circumferential groove for retaining the bearing insert adjacent the inner surface of the outer shell.

20. An acetabular cup prosthesis assembly according to claim 19, wherein said lip means formed in the outer surface of the bearing insert comprises an outwardly extending lip having a generally horizontal surface which extends into the second groove and which interacts with a surface of the groove to retain the bearing insert adjacent the inner surface of the outer shell.

21. An acetabular cup prosthesis, comprising:
   a cup shaped outer shell having an outer surface and an inner surface;
   a cup-shaped bearing insert having an outer surface, an inner surface, and an opening defined generally by the intersection of said outer and inner surfaces, said opening having a relatively small first diameter and being elastically expandable to a relatively larger second diameter;
   retaining means for retaining the cup-shaped bearing insert within the cup-shaped outer shell;
   collar means, movable from a disengaged position to an engaged position adjacent the outer surface of the bearing insert, for preventing said opening from expending to said second diameter; and
   locking means, separable from said collar means, for securing said collar means in the engaged position, at least a portion of said locking means extending outwardly from the inner surface of the outer shell to engage and secure said collar means in the engaged position, said portion being elastically deformable inwardly toward the inner surface of the outer shell to allow the collar means to be moved between the engaged and disengaged positions.

22. An acetabular cup prosthesis according to claim 21, wherein said outer shell has a first circumferential groove formed in the inner surface thereof, and wherein said locking means comprises a locking ring disposed in said first circumferential groove.

23. An acetabular cup prosthesis, comprising:
   a cup shaped outer shell having an outer surface and an inner surface;
   a cup-shaped bearing insert having an outer surface, an inner surface, and an opening defined generally by the intersection of said outer and inner surfaces, said opening having a relatively small first diameter and being elastically expandable to a relatively larger second diameter;
   retaining means for retaining the cup-shaped bearing insert within the cup-shaped outer shell;
   collar means, movable from a disengaged position to an engaged position adjacent the outer surface of the bearing insert, for preventing said opening from expanding to said second diameter; and
   locking means for securing said collar means in the engaged position, at least a portion of said locking means extending outwardly from the inner surface of the outer shell to engage and secure said collar means in the engaged position, said portion being elastically deformable inwardly toward the inner surface of the outer shell to allow the collar means to be moved between the engaged and disengaged positions;

wherein said outer shell has a first circumferential groove formed in the inner surface thereof, and wherein said locking means comprises a locking ring disposed in said first circumferential groove; and second retaining means for preventing rotational movements of the locking ring so as to maintain the ring in a fixed orientation relative to the outer shell.

24. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

first retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert;

locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said means collar to be selectively moved to the disengaged and engaged positions; and second retaining means for preventing rotational movement of said locking means in said first circumferential groove, wherein said second retaining means comprises a split in said locking means, and comprising pin means secured to the outer shell and protruding into the first circumferential groove so as to engage surfaces of said split.

25. An acetabular cup prosthesis according to claim 24, wherein said pin means secured to the outer shell comprises a pin extending from the outer surface to the inner surface of the outer shell and into the first circumferential groove.

26. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert; and locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said means collar to be selectively moved to the disengaged and engaged positions;

wherein said protruding portion of said locking means comprises a plurality of tabs formed in generally opposing relation on said locking means.

27. An acetabular cup prosthesis according to claim 26, further comprising second retaining means for preventing rotational movement of said locking means so as to maintain the orientation of said tabs relative to the outer shell.

28. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert within the opening in the outer shell;

collar means, movable from a disengaged position to an engaged position adjacent the outer surface of the bearing insert, for preventing said opening from expanding to said second diameter so as to allow the femoral head to be locked into place within the insert; and locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said means collar to be selectively moved to the disengaged and engaged positions;

wherein said protruding portion of said locking means has an inwardly facing surface which interacts with an outwardly facing surface of the collar means to secure said collar means in the engaged position adjacent the outer surface of the bearing insert, and an outwardly facing beveled surface to facilitate deformation of said protruding portion inwardly into the first circumferential groove; and wherein said collar means has a beveled surface which interacts with the beveled surface on the locking means to facilitate deformation of said protruding portion inwardly into the first circumferential groove to allow said collar means to be moved into the engaged position adjacent the outer surface of the bearing insert.

29. An acetabular cup prosthesis assembly, comprising: a sub-assembly which includes:

an outer shell having an outer surface and an inner surface;

a bearing insert having an outer surface, an inner surface, and an opening defined by an edge surface joining said outer and inner surfaces, said opening having a relatively small first diameter and being elastically expandable to a relatively larger second diameter;

retaining means for retaining the outer surface of the bearing insert adjacent the inner surface of the outer shell;

locking means disposed on the inner surface of the outer shell, at least a portion of said locking means protruding outwardly from said inner surface of said shell, said portion being elastically deformable inwardly toward said inner surface; and collar means, movable from a disengaged position to an engaged position adjacent the outer surface of the bearing insert, for preventing said opening from expanding to said second diameter, said collar means interacting with the protruding portion of said locking means to secure the collar means in said engaged position adjacent the outer surface of the bearing insert;

wherein said outer shell has a first circumferential groove formed in the inner surface thereof, and wherein said locking means comprises a locking ring disposed in said first circumferential groove; and wherein said collar means has a beveled surface facing inwardly toward the inner surface of the outer shell, and a generally horizontal surface facing outwardly from the inner surface of the outer shell, and wherein said beveled surface interacts with a beveled surface of the protruding portion of the locking ring to facilitate elastic deformation of said portion when the collar means is moved into the engaged position adjacent the outer surface of the bearing insert, and wherein said generally horizontal surface interacts with a generally horizontal surface of the protruding portion of the locking ring when the collar means reaches the engaged position to retain the collar means in said position.

30. An acetabular cup prosthesis assembly, comprising: a sub-assembly which includes:

an outer shell having an outer surface and an inner surface;

a bearing insert having an outer surface, an inner surface, and an opening defined by an edge surface joining said outer and inner surfaces, said opening having a relatively small first diameter and being elastically expandable to a relatively larger second diameter;

first retaining means for retaining the outer surface of the bearing insert adjacent the inner surface of the outer shell;

locking means disposed on the inner surface of the outer shell, at least a portion of said locking means protruding outwardly from said inner surface of said shell, said portion being elastically deformable inwardly toward said inner surface; and collar means, movable from a disengaged position to an engaged position adjacent the outer surface of the bearing insert, for preventing said opening from expanding to said second diameter, said collar means interacting with the protruding portion of said locking means to secure the collar means in said engaged position adjacent the outer surface of the bearing insert;

wherein said outer shell has a first circumferential groove formed in the inner surface thereof, and wherein said locking means comprises a locking ring disposed in said first circumferential groove; and second retaining means for preventing rotational movements of the locking ring so as to maintain the protruding portion of the ring in a fixed orientation relative to the outer shell; and wherein said second retaining means comprises a split in said ring, and pin means in the first circumferential groove for engaging surfaces of said split to prevent rotation of the ring.

31. An acetabular cup prosthesis for receiving and releasably retaining a femoral head component of a hip prosthesis, comprising:

an outer shell having a generally smooth hemispherical outer surface, an inner surface, an opening defined by a peripheral edge surface joining said outer and inner surfaces, and a first circumferential groove formed in said inner surface;

a bearing insert, adapted to be received within the opening in the outer shell, having an outer surface, an inner surface, and an opening defined by a peripheral edge surface joining said outer and inner surfaces, wherein said inner surface and said opening are adapted to receive the femoral head of the hip prosthesis, and wherein said opening has a first diameter which is smaller than a diameter of the femoral head, and wherein said opening is elastically expandable to a second diameter to allow for passage of the femoral head through said opening;

retaining means for retaining said bearing insert with the opening in the outer shell;

collar means, movable from a disengaged position to an engaged position adjacent the outer surface of the bearing insert, for preventing said opening from expanding to said second diameter so as to allow the femoral head to be locked into place within the insert; and locking means disposed in said first circumferential groove in the inner surface of said outer shell, at least a portion of said locking means protruding outwardly from said groove beyond the inner surface of said shell so as to interact with a portion of said collar means to secure said collar means in the engaged position adjacent the outer surface of the bearing insert, said portion of said locking means being elastically deformable inwardly into said groove so as to allow said collar means to be selectively moved to the disengaged and engaged positions;

wherein said protruding portion of said locking means has an inwardly facing surface which interacts with an outwardly facing surface of the collar means to secure said collar means in the engaged position adjacent the outer surface of the bearing insert, and an outwardly facing beveled surface to facilitate deformation of said protruding portion inwardly into the first circumferential groove; and wherein said collar means has a beveled surface which interacts with the beveled surface on the locking means to facilitate deformation of said protruding portion inwardly into the first circumferential groove to allow said collar means to be moved in to the engaged position adjacent the outer surface of the bearing insert.

* * * * *